United States Patent
Schneider et al.

(10) Patent No.: US 11,739,042 B2
(45) Date of Patent: Aug. 29, 2023

(54) PROCESS FOR HYDROFORMYLATION OF OLEFINS USING PT AND IODINE OR BROMINE

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 18/064,948

(22) Filed: Dec. 13, 2022

(65) Prior Publication Data
US 2023/0192583 A1    Jun. 22, 2023

(30) Foreign Application Priority Data

Dec. 17, 2021 (EP) .................................... 21215374

(51) Int. Cl.
*C07C 45/50* (2006.01)
*B01J 31/24* (2006.01)
*B01J 37/04* (2006.01)

(52) U.S. Cl.
CPC ......... *C07C 45/505* (2013.01); *B01J 31/2457* (2013.01); *B01J 37/04* (2013.01); *B01J 2231/321* (2013.01); *B01J 2531/828* (2013.01)

(58) Field of Classification Search
CPC .......................... C07C 45/505; B01J 31/2457
See application file for complete search history.

(56) References Cited

PUBLICATIONS

Botteghi. C. et al. Synthesis of 2-chromanol by hydroformylation of 2-hydroxystyrene derivatives. Journal of Molecular Catalysis A: Chemical 200. 2003, pp. 147-156.
U.S. Appl. No. 18/064,945, filed Dec. 13, 2022, Schneider et al.
U.S. Appl. No. 18/064,946, filed Dec. 13, 2022, Schneider et al.
U.S. Appl. No. 18/064,947, filed Dec. 13, 2022, Schneider et al.
U.S. Appl. No. 18/064,949, filed Dec. 13, 2022, Schneider et al.
U.S. Appl. No. 18/064,950, filed Dec. 13, 2022, Schneider et al.
U.S. Appl. No. 18/064,952, filed Dec. 13, 2022, Schneider et al.
U.S. Appl. No. 18/064,953, filed Dec. 13, 2022, Schneider et al.
U.S. Appl. No. 18/064,955, filed Dec. 13, 2022, Schneider et al.
U.S. Appl. No. 18/064,958, filed Dec. 13, 2022, Schneider et al.
European Search Report dated Jul. 19, 2022 for European Patent Application No. 21215374.6 (5 pages in German with machine translation).
Van der Veen, Lars. A., et al. Wide bite angle amine, arsine and phosphine ligands in rhodium and platinum/tin-catalysed hydroformylation. J. Chem. Soc., Dalton Trans. 2000, pp. 2105-21120.

*Primary Examiner* — Sikarl A Witherspoon
(74) *Attorney, Agent, or Firm* — Smith, Gambrell & Russell, LLP

(57) ABSTRACT

Process for hydroformylation of olefins using Pt and iodine or bromine.

15 Claims, No Drawings

PROCESS FOR HYDROFORMYLATION OF OLEFINS USING PT AND IODINE OR BROMINE

The present invention relates to a process for hydroformylation of olefins using Pt and iodine or bromine.

C. Botteghi et al., Journal of Molecular Catalysis A: Chemical 200, (2003), 147-156 describes the use of Pt(Xantphos)$Cl_2$ for hydroformylation of 2-tosyloxystyrene.

The problem addressed by the present invention is that of providing a novel hydroformylation process. The process here is to afford an increased yield compared to the process known from the prior art using Pt with $Cl_2$.

This object is achieved by a process according to claim 1.

Process comprising the process steps of:
a) initially charging an olefin;
b) adding a compound of formula (I):

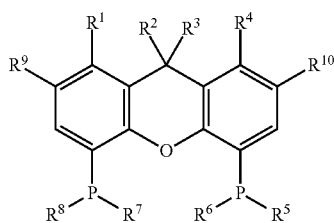

where $R^1$, $R^2$, $R^3$, $R^4$, $R^5$, $R^6$, $R^7$, $R^8$ are selected from: —H, —($C_1$-$C_{12}$)-alkyl, —($C_6$-$C_{20}$)-aryl, and $R^9$, $R^{10}$ are selected from: —($C_1$-$C_{12}$)-alkyl, —($C_6$-$C_{20}$)-aryl, and, if $R^1$, $R^2$, $R^3$, $R^4$, $R^5$, $R^6$, $R^7$, $R^8$, $R^9$, $R^{10}$ are —($C_6$-$C_{20}$)-aryl, the aryl ring may have substituents selected from: —($C_1$-$C_{12}$)-alkyl, —O—($C_1$-$C_{12}$)-alkyl;

c) adding a Pt compound capable of forming a complex;
d) adding an iodine compound or bromine compound;
e) feeding in CO and $H_2$;
f) heating the reaction mixture from steps a) to e), to convert the olefin to an aldehyde.

In this process, process steps a) to e) can be effected in any desired sequence. Typically, however, CO and $H_2$ are added after the co-reactants have been initially charged in steps a) to d).

It is possible here for process steps c) and d) to be effected in one step by adding $PtI_2$ or $PtBr_2$. In a preferred variant of the process, the Pt compound and the iodine compound or bromine compound are added in one step by adding $PtI_2$ or $PtBr_2$.

The expression ($C_1$-$C_{12}$)-alkyl encompasses straight-chain and branched alkyl groups having 1 to 12 carbon atoms. These are preferably ($C_1$-$C_8$-alkyl groups, more preferably ($C_1$-$C_6$)-alkyl, most preferably ($C_1$-$C_4$)-alkyl.

Suitable ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression ($C_6$-$C_{20}$)-aryl encompasses mono- or polycyclic aromatic hydrocarbyl radicals having 6 to 20 carbon atoms. These are preferably ($C_6$-$C_{14}$)-aryl, more preferably ($C_6$-$C_{10}$)-aryl.

Suitable ($C_6$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred $C_6$-$C_{20}$-aryl groups are phenyl, naphthyl and anthracenyl.

In one variant of the process, $R^2$, $R^3$, $R^5$, $R^6$, $R^7$, $R^8$ are selected from: —($C_1$-$C_{12}$)-alkyl, -($C_6$-$C_{20}$)-aryl.

In one variant of the process, $R^5$, $R^6$, $R^7$, $R^8$ are —($C_6$-$C_{20}$)-aryl.

In one variant of the process, $R^5$ and $R^6$ are different radicals and $R^7$ and $R^8$ are different radicals.

In one variant of the process, $R^2$ and $R^3$ are —($C_1$-$C_{12}$)-alkyl.

In one variant of the process, $R^2$ and $R^3$ are —$CH_3$.

In one variant of the process, $R^1$ and $R^4$ are each —H.

In one variant of the process, $R^9$ and $R^{10}$ are —($C_1$-$C_{12}$)-alkyl.

In one variant of the process, $R^9$ and $R^{10}$ are —$^tBu$.

In one variant of the process, the compound (I) has the structure (1):

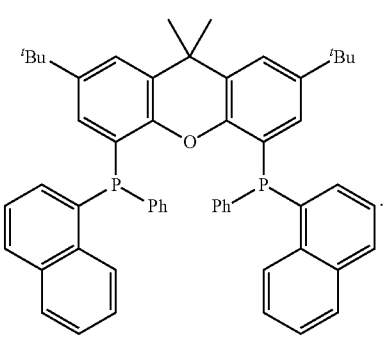

In one variant of the process, the Pt compound is selected from: Pt(II)$I_2$, Pt(II)$Br_2$, Pt(IV)$I_4$, Pt(IV)$Br_4$, diphenyl(1,5-COD)Pt(II), Pt(II)(acac)$_2$, Pt(0)(PPh$_3$)$_4$, Pt(0)(DVTS) solution (CAS:68478-92-2), Pt(0)(ethylene)(PPh$_3$)$_2$, Pt(II)$Br_2$ (COD), tris(benzylideneacetone)Pt(0), Pt(II)(OAC)$_2$ solution, Pt(0)(t-Bu)$_2$, Pt(II)(COD)Me$_2$, Pt(II)(COD)$I_2$, Pt(IV)IMe$_3$, Pt(II)(hexafluoroacetylacetonate)$_2$.

In one variant of the process, the Pt compound is selected from: Pt(III)$I_2$, Pt(II)$Br_2$.

In one variant of the process, the iodine compound or the bromine compound is selected from: alkali metal halide, alkaline earth metal halide, $NH_4X$, alkylammonium halide, dialkyl halide, trialkyl halide, tetraalkyl halide, cycloalkylammonium halide.

In one variant of the process, an iodine compound is added in process step d).

In one variant of the process, the iodine compound is Pt(II)$I_2$.

In one variant of the process, the iodine compound is added in an amount in the range of 0.1 to 10, measured in equivalents based on Pt.

In one variant of the process, a bromine compound is added in process step d).

In one variant of the process, the bromine compound is Pt(II)$Br_2$.

In one variant of the process, the bromine compound is added in an amount in the range of 0.1 to 10, measured in equivalents based on Pt.

In one variant of the process, this process comprises the additional process step e'): e') adding a solvent.

In one variant of the process, the solvent is selected from: THF, DCM, ACN, heptane, DMF, toluene, texanol, pentane, hexane, octane, isooctane, decane, dodecane, cyclohexane, benzene, xylene, Marlotherm, propylene carbonate, MTBE, diglyme, triglyme, diethyl ether, dioxane, isopropanol, tert-butanol, isononanol, isobutanol, isopentanol, ethyl acetate.

In one variant of the process, the solvent is selected from: THF, DCM, ACN, heptane, DMF, toluene, texanol.

In one variant of the process, CO and $H_2$ is fed in at a pressure in a range from 1 MPa (10 bar) to 6 MPa (60 bar).

In one variant of the process, CO and $H_2$ is fed in at a pressure in a range from 1 MPa (20 bar) to 6 MPa (50 bar).

In one variant of the process, the mixture is heated at a temperature in the range from 25° C. to 150° C.

In one variant of the process, the mixture is heated at a temperature in the range from 30° C. to 130° C.

In one variant of the process, the olefin is selected from: ethene, propene, 1-butene, cis-and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

The invention shall be elucidated in more detail hereinbelow with reference to working examples.

EXPERIMENTAL DESCRIPTION

A vial was charged with $PtX_2$ (X=halogen), ligand, and an oven-dried stirrer bar. The vial is then sealed with a septum (PTFE-coated styrene-butadiene rubber) and phenolic resin cap. The vial is evacuated and refilled with argon three times. Toluene and 1-octene were added to the vial using a syringe. The vial was placed in an alloy plate, which was transferred to an autoclave of the 4560 series from Parr Instruments under an argon atmosphere. After purging the autoclave three times with $CO/H_2$, the synthesis gas pressure was increased to 40 bar at room temperature. The reaction was conducted at 80° C. for 18 h. On termination of the reaction, the autoclave was cooled to room temperature and cautiously decompressed. Yield and selectivity were determined by GC analysis.

Variation of the Halogen

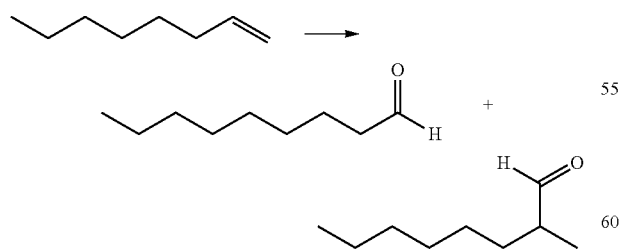

Reaction Conditions:

1.0 mmol of 1-octene, 0.5 mol % of $PtX_2$, 2.0 equivalents of ligand (1), solvent: toluene, $p(CO/H_2)$: 40 bar, T: 80° C., t: 18 h.

Yields:

| Ligand | Halogen | Yield [%] |
|---|---|---|
| 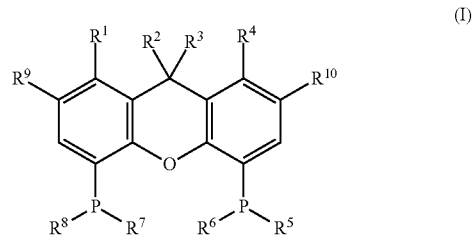 (1) | I/Br/Cl | 96/24/0 |

As the experimental results show, the object is achieved by the process according to the invention.

The invention claimed is:

1. A process comprising the process steps of:
   a) initially charging an olefin;
   b) adding a compound of formula (I):

(I)

where $R^1$, $R^2$, $R^3$, $R^4$, $R^5$, $R^6$, $R^7$ and $R^8$ are selected from: —H, —($C_1$-$C_{12}$)-alkyl or —($C_6$-$C_{20}$)-aryl, and
   $R^9$ and $R^{10}$ are selected from: —($C_1$-$C_{12}$)-alkyl or —($C_6$-$C_{20}$)-aryl,
   and, if $R^1$, $R^2$, $R^3$, $R^4$, $R^5$, $R^6$, $R^7$, $R^8$, $R^9$, $R^{10}$ are —($C_6$-$C_{20}$)-aryl, the aryl ring may have substituents selected from: —($C_1$-$C_{12}$)-alkyl or —O—($C_1$-$C_{12}$)-alkyl;
   c) adding a Pt compound capable of forming a complex;
   d) adding an iodine compound or bromine compound;
   e) feeding in CO and $H_2$;
   f) heating the reaction mixture from steps a) to e), to convert the olefin to an aldehyde.

2. The process according to claim 1, where $R^2$, $R^3$, $R^5$, $R^6$, $R^7$, $R^8$ are selected from: —($C_1$-$C_{12}$)-alkyl or —($C_6$-$C_{20}$)-aryl.

3. The process according to claim 1, where $R^5$, $R^6$, $R^7$, $R^8$ are —($C_6$-$C_{20}$)-aryl.

4. The process according to claim 1, where $R^2$ and $R^3$ are —($C_1$-$C_{12}$)-alkyl.

5. The process according to claim 1, where $R^1$ and $R^4$ are each —H.

6. The process according to claim 1, where $R^9$ and $R^{10}$ are —($C_1$-$C_{12}$)-alkyl.

7. The process according to claim 1,
wherein the compound (I) has the structure (1):

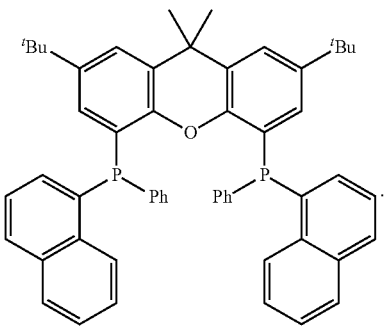

8. The process according to claim 1,
wherein the Pt compound is selected from: Pt(II)I$_2$, Pt(II)Br$_2$, Pt(IV)I$_4$, Pt(IV)Br$_4$, diphenyl(1,5-COD)Pt(II), Pt(II)(acac)$_2$, Pt(0)(PPh$_3$)$_4$, Pt(0)(DVTS) solution (CAS:68478-92-2), Pt(0)(ethylene)(PPh$_3$)$_2$, Pt(II)Br$_2$(COD), tris(benzylideneacetone)Pt(0), Pt(II)(OAC)$_2$ solution, Pt(0)(t-Bu)$_2$, Pt(II)(COD)Me$_2$, Pt(II)(COD)I$_2$, Pt(IV)IMe$_3$ or Pt(II)(hexafluoroacetylacetonate)$_2$.

9. The process according to claim 1,
wherein an iodine compound is added in process step d).

10. The process according to claim 9,
wherein the iodine compound is added in an amount in the range of 0.1 to 10, measured in equivalents based on Pt.

11. The process according to claim 1,
wherein a bromine compound is added in process step d).

12. The process according to claim 11,
wherein the bromine compound is added in an amount in the range of 0.1 to 10, measured in equivalents based on Pt.

13. The process according to claim 1,
comprising the additional process step e'):
e') adding a solvent.

14. The process according to claim 1,
wherein CO and H$_2$ is fed in at a pressure in a range from 1 MPa (10 bar) to 6 MPa (60 bar).

15. The process according to claim 1,
wherein the reaction mixture is heated to a temperature in the range from 25° C. to 150° C.

* * * * *